(12) United States Patent
Maurer

(10) Patent No.: US 8,778,102 B2
(45) Date of Patent: Jul. 15, 2014

(54) POST LASER DRILLING STRESS RELIEF OF SURGICAL NEEDLES MADE OF REFRACTORY ALLOYS

(75) Inventor: Robert E. Maurer, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 1119 days.

(21) Appl. No.: 12/139,744

(22) Filed: Jun. 16, 2008

(65) Prior Publication Data

US 2009/0312720 A1     Dec. 17, 2009

(51) Int. Cl.
*C22F 1/18* (2006.01)
*A61M 5/32* (2006.01)
*B21G 3/18* (2006.01)

(52) U.S. Cl.
USPC ................. 148/668; 604/272; 163/5

(58) Field of Classification Search
USPC ............. 604/273, 272; 148/559, 668; 163/5
See application file for complete search history.

(56) References Cited

U.S. PATENT DOCUMENTS

| 3,394,704 A | 7/1968 | Dery |
| 3,835,912 A | 9/1974 | Kristensen et al. |
| 5,012,066 A | 4/1991 | Matsutani et al. |
| 5,415,707 A | 5/1995 | Bendel et al. |
| 5,776,268 A * | 7/1998 | McJames et al. ............. 148/656 |
| 7,001,472 B2 | 2/2006 | Collier et al. |
| 2008/0147117 A1* | 6/2008 | Cichocki et al. ............. 606/223 |

FOREIGN PATENT DOCUMENTS

| EP | 0650698 A | 5/1995 |
| EP | 1396305 A | 3/2004 |
| RU | 2218879 C | 12/2003 |
| WO | WO 2007100127 A1 | 9/2007 |
| WO | WO 2008/151108 A | 12/2008 |

OTHER PUBLICATIONS

Shields et al., Heat Treating of Refractory Metals and Alloys, ASM Handbook, ASM International, vol. 4, 1991, p. 1-3.*
International Search Report dated Sep. 11, 2009 for International Appln. No. PCT/US2009/046570.
RD40224 Mechanical Positioning and Laser Drilling of Surgical Suture Needles, Research Disclosure, Oct. 1997, pp. 708-711.

\* cited by examiner

*Primary Examiner* — Roy King
*Assistant Examiner* — Caitlin Kiechle
(74) *Attorney, Agent, or Firm* — E. Richard Skula

(57) ABSTRACT

A method of stress relieving drilled surgical needles is disclosed. At least the metal about a drilled bore hole is heat treated to relieve stress without annealing.

12 Claims, 3 Drawing Sheets

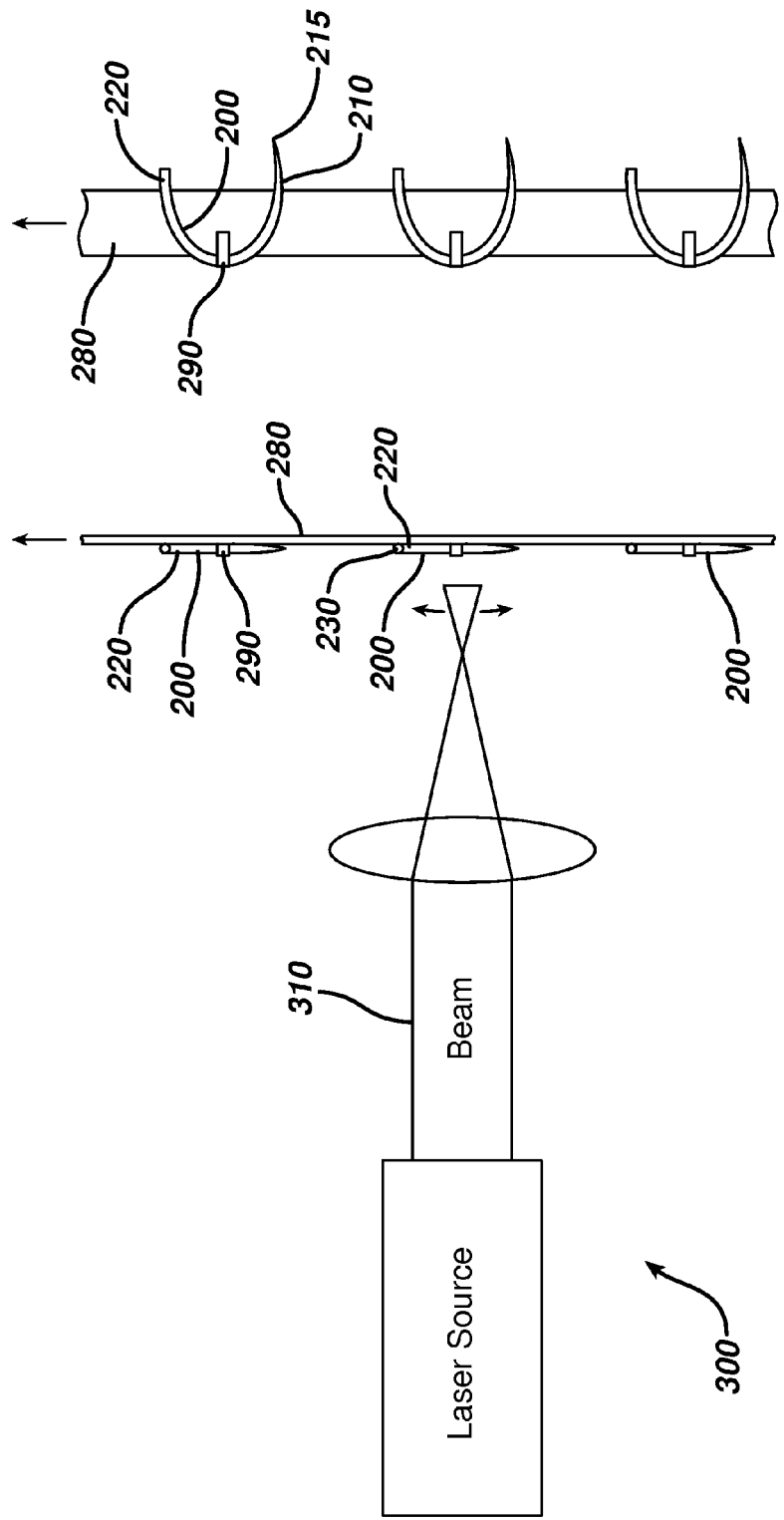

POST LASER DRILLING STRESS RELIEF OF SURGICAL NEEDLES MADE OF REFRACTORY ALLOYS

FIELD OF THE INVENTION

The field of art to which this invention pertains is surgical needles, more specifically, methods of manufacturing surgical needles.

BACKGROUND OF THE INVENTION

Surgical needles and methods of manufacturing surgical needles are known in the art. Surgical needles are typically made from conventional biocompatible metals such as stainless steels. The selection of the materials used to manufacture the surgical needles depends upon a variety of factors including manufacturability, machineablility, cost, biocompatibility, and mechanical properties. Conventional surgical needles are made utilizing conventional manufacturing processes. Typically, a wire made from a biocompatible metal is drawn in a conventional wire mill to obtain a wire having a desired diameter or wire size. The wire is then cut into pieces known as needle blanks having a desired length, and the needle blanks are then processed through a series of conventional manufacturing process steps including bending, forming, grinding, polishing, heat treating, coating, etc.

A conventional surgical needle has a distal piercing point and a proximal suture mounting section. The proximal suture mounting sections are typically a channel formed in the proximal end or a bore hole drilled into the proximal end. If a bore hole is used, it is typically formed by conventional mechanical drilling or laser drilling processes. Suture mounting is accomplished by inserting an end of a surgical suture into the channel or into the bore hole, and then mechanically compressing a section of the proximal end of the surgical needle about the end of the suture using any of a variety of conventional processes known in the art as swaging. The degree of swaging will depend upon the desired release characteristics i.e., the amount of force necessary to detach the suture from the channel or bore hole.

There is a constant need in this art for improved surgical needles having improved performance characteristics. It is desirable to have a surgical needle made from a wire having a diameter as close as possible to that of the suture to which it is attached. This can be accomplished by having a needle with the smallest cross-section possible (made from a wire having a small wire size) while providing sufficient resistance to bending when a surgeon grasps the needle and passes it through tissue. While existing surgical needles made from conventional stainless steels have such properties, novel needles made from materials such as refractory metal alloys have been developed that have maximized such characteristics. Since these materials are typically harder than conventional stainless steel alloys and have other differing metallurgical characteristics including greater strength, higher elastic modulus, and desirable magnetic properties, novel processes are needed to manufacture such needles and to manufacture needle-suture combinations utilizing such needles. For example, it is known that swaging a surgical suture to a drilled refractory alloy surgical needle may result in cracking about the proximal end of the needle.

SUMMARY OF THE INVENTION

Accordingly, a novel method of processing a laser-drilled surgical needle is disclosed. In the method of the present invention, a surgical needle made from a refractory alloy or stainless steel is provided. The needle has a distal end and a proximal end. A bore hole is drilled into the proximal end of the needle using a laser drilling apparatus. The needle, or just the suture mounting end or section of the surgical needle, is then subjected to an elevated temperature for a sufficient period of time to relieve residual stresses in the metal of the proximal end or section of the surgical needle surrounding the bore hole. The time and temperature are selected to be sufficiently effective such that stress relief is effected without softening the metal.

Yet another aspect of the present invention is a novel surgical needle. The surgical needle has a body having a distal piercing point and a proximal suture mounting section. The needle has a bore hole that is laser-drilled in the proximal suture mounting section. The needle is processed using the above-described novel heat treating process to relieve residual stresses.

It is now possible, using the process of the present invention, to swage surgical sutures to surgical needles made from refractory metal alloys without attendant cracking of the swaged portion of the needle.

These and other aspects and advantages of the present invention will become more apparent from the following description and accompanying drawings.

BRIEF DESCRIPTION OF THE DRAWINGS

FIG. 3 is a schematic diagram illustrating the process of the present invention wherein surgical needles mounted to a strip are heat treated.

FIG. 3A is a partial plan view of the strip containing needles of FIG. 3.

DETAILED DESCRIPTION OF THE INVENTION

The novel process of the present can be utilized with surgical needles made from alloys of refractory metals including tungsten, molybdenum, niobium, tantalum, and rhenium. Surgical needles made from tungsten-rhenium alloys are disclosed in the following references which are incorporated by reference: U.S. Pat. No. 5,415,707 (Bendel et al.) U.S. patent application Ser. Nos. 11/611,353; 11/611,387; 11/756,668; and, and Ser. No. 11/756,679. Although not preferred, the method of the present invention may also be used with laser drilled surgical needles made from conventional stainless steel alloys.

Figure 1:
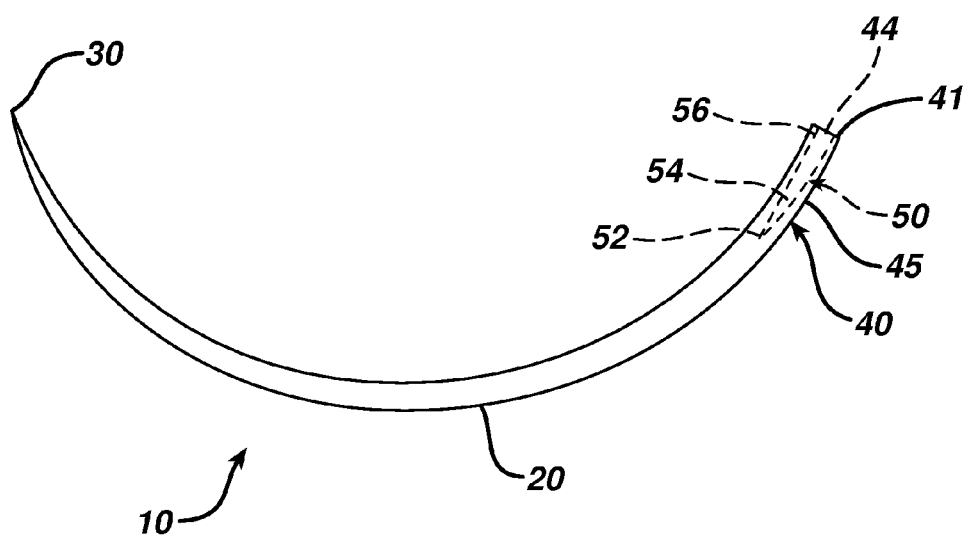
FIG. 1 is a plan view of a drilled surgical needle made from a refractory alloy.

Referring now to FIG. 1, a drilled surgical needle 10 made from a tungsten-rhenium refractory alloy is illustrated. The needle 10 is seen to have a body 20 made from a tungsten rhenium alloy wire. The needle 10 has a distal piercing point 30 and proximal needle mounting section 40 having end 41. A suture mounting bore hole 50 is contained in section 40. Bore hole 50 is seen to have distal end 52, cavity 54 and proximal end 56 in communication with opening 44 in end 41.

The needle 10 may be made using conventional manufacturing processes that are adapted to manufacturing surgical needles made from refractory metal alloys. Typically, in a conventional process, wire made from the desired metal alloy is drawn in a wire mill to a desired diameter. The wire is then cut in conventional wire cutting equipment to produce needle blanks having the desired length. The wire then goes through a series of conventional manufacturing process steps including forming, grinding, polishing, cleaning and drilling.

Needle blanks may be drilled in several ways. The blanks may be mounted in a fixture and a conventional mechanical drill may be used to drill out a bore hole in the proximal end of the needle blank. Although mechanical drilling may be useful to drill bore holes in surgical needles, there are limitations associated with such a drilling process. For example, drills wear out and need to be replaced on a constant basis. In addition, the mechanical drilling process is time consuming and is less desirable for high speed, automated production processes. In addition, mechanical drills cannot typically be used in a cost effective manner for drilling needles made from very hard materials, or those that readily work-harden during the drilling operation. Laser drilling systems have been developed for drilling bore holes in surgical needles. These laser systems typically use Nd:YAG lasers, but any laser type capable of providing the required power density and being focused to the required spot size would be acceptable. Specific cycles are utilized to obtain the desired bore hole diameter and depth by controlling laser beam parameters including beam power, energy density, energy density distribution, pulse shape, pulse duration, and the number of pulses.

Figure 2:
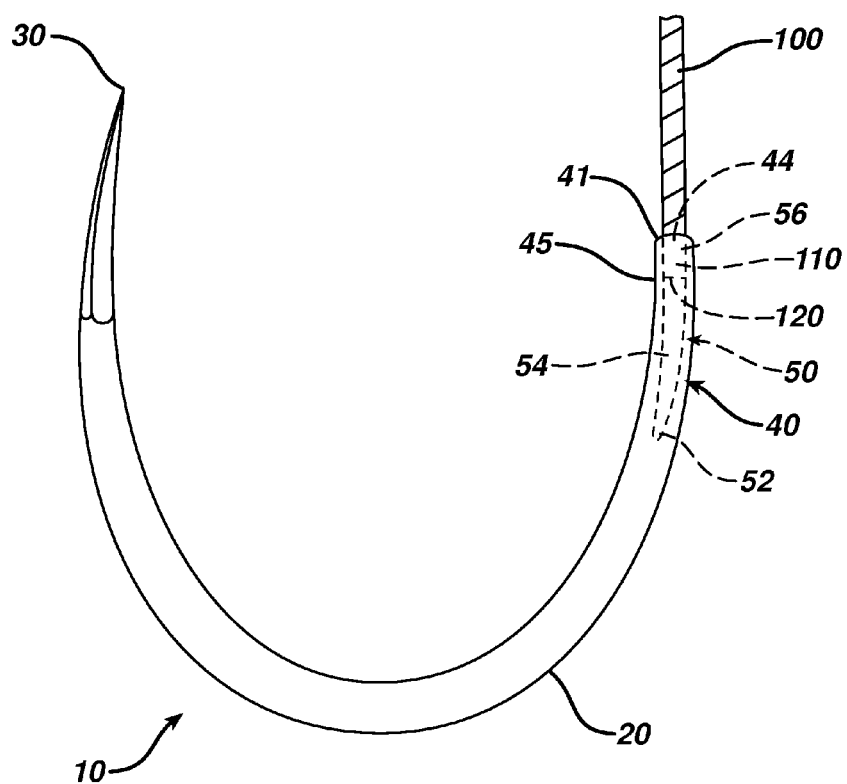
FIG. 2 illustrates the needle of FIG. 1 with a suture mounted to the bore hole of the needle after treatment with the process of the present invention.

Referring now to FIG. 2, the drilled refractory alloy surgical needle 10 of FIG. 1 is seen having a surgical suture 100 mounted thereto. The surgical suture is seen to have proximal end 110 mounted in cavity 54 of bore hole 50 and free proximal end 120. The surgical suture 110 is mounted to proximal needle mounting section 40 using a conventional mechanical swaging die and process and equivalents. This results in the swage section 45 in needle mounting section 40, which prevents the release of the end 110 from bore hole 50 or provides a controlled release at a predetermined force. The suture 100 can be selected from a variety of conventional surgical sutures.

In order to swage a surgical suture to a drilled surgical needle, the needle is mounted in a die and a tool is pressed against a section of the suture mounting section of the needle. This causes a deformation of the metal such that the end of a suture inserted into the drilled bore hole is compressed within the cavity of the hole. Although such a process works well with conventional surgical needles, using such a swaging process with harder metals such as the refractory metal alloys may result in cracking of the needle about the suture mounting bore hole. Such cracking precludes the use of mechanical swaging with such needles. Mechanical swaging is an optimal method of attaching surgical sutures to drilled surgical needles. Other known methods such as glues or cements have disadvantages including lower suture attachment strength, difficulties associated with inserting adhesives into the blind bore hole due to air entrapment, and being an excessively time consuming process.

The process of the present invention facilitates laser drilled refractory alloy surgical needles to be processed with mechanical swaging suture attachment processes. The process of the present invention involves heating either the portion of the needle containing the laser drilled hole, or the entire needle, for a sufficient time at a sufficient temperature to effectively relieve residual stresses in the metal surrounding the laser drilled bore hole. These residual stresses are believed to result from the enormously steep thermal gradient experienced during laser drilling, and a very thin layer of recast metal lining the inside surface of the hole. When the recast layer solidifies and cools, it is believed that its thermal contraction is restrained by the relatively unheated metal adjacent to the hole. This results in a state of residual tensile stress within the recast layer.

If not relieved, as by the process of the present invention, cracks are likely to originate within this area of residual tensile stress during the mechanical swaging process used for suture attachment. For laser drilled surgical needles made of tungsten-rhenium alloys, the stress relief cycle (in an atmosphere controlled furnace) is preferably ranges from 900-1100 degrees Centigrade, for 15-60 minutes at temperature. This provides for stress relief, without softening the tungsten-rhenium or inducing microstructural alteration. If it were desired to heat only the region of the surgical needle containing the bore hole for stress relief, as by laser, induction heating or the like, higher temperatures for shorter periods of time would typically be required. To be consistent with the teachings of this invention, temperature-time selection would be bound from above by that which would result in microstructural and/or hardness changes in the needle alloy.

An example of an automated process of the present invention for relieving stress in laser drilled needles is schematically illustrated in FIG. 3 and FIG. 3A. As seen in FIGS. 3 and 3A, needle blanks 200 are mounted to a moveable strip 280 by crimps or tabs 290. In place of a strip, the needle blank 200 may be mounted to a conventional fixture. Each needle blank 200 is seen to have distal section 210 with piercing point 215 and proximal needle mounting section 220. A bore hole 230 has been laser-drilled into section 220. A conventional laser drilling system 300 is located proximate to the needle blank 200 and strip 280 such that laser beam 310 may be directed to proximal needle mounting section 220 or the entire length of the needle blank 200 as the strip 280 moves the needle blanks 200 into position in front of beam 310. The beam 310 is moveable and has sufficient energy and is maintained on the section 220 or the entire needle blank 200 for a sufficient amount of time such that the metal in section 220 surrounding bore hole 230 is effectively stress relieved without annealing the metal. Lasers which may be useful in the stress relief process of the present invention will include conventional lasers such as the Nd:YAG, $CO_2$, and fiber lasers, and other equivalent types capable of generating the required amount of heating over the required time interval for residual stress relief. Those skilled in the art will appreciate that the time that the suture mounting sections of the needles are exposed to the laser energy will depend upon several factors, including beam power, energy density, and energy density distribution, for example, and not being limited to any particular range of times, the time that the laser beam energy is applied may range from about 1 milliseconds to about a few seconds. Those skilled in the art will appreciate that the times will vary in accordance with the previously describe parameters. Other methods of heating the metal in the needles useful in the stress relieving process of the present invention will include conventional heating methods such as inductive heating and resistive heating.

After being treated by the stress relief process of the present invention, the refractory alloy surgical needles will readily be able to have surgical sutures attached to the suture mounting ends using mechanical swaging without cracking. The metal in the stress relieved area can be metallurgically characterized by being unaltered with respect to microstructure and hardness. In contrast, an annealing process produces a metallurgical profile characterized by reduced hardness. It is surprising and unexpected that the process of the present invention for treating surgical needles would prevent cracking since laser drilled needles made of stainless steel do not exhibit the same propensity to crack during suture attachment by mechanical swaging. Annealing (softening) processes would be disadvantageous for use in treating the suture mounting ends of drilled surgical needles made from tungsten-rhenium alloys, and other refractory alloys, because, counter to the behavior of steels, which exhibit increasing ductility with decreasing hardness, tungsten-rhenium alloys lose ductility with decreasing hardness.

The following examples are illustrative of the principles and practice of the present invention although not limited thereto.

Example 1

Tungsten-Rhenium alloy wire having a diameter of 0.01-inch was cut into needle blanks using conventional cutting equipment. The alloy composition was 74.25% tungsten+ 25.75% rhenium. The needle blanks were pointed, polished and curved in a conventional manner. The proximal ends of the needle blanks were drilled to form bore holes using a conventional needle-drilling Nd:YAG laser. Conventional polyester suture was mounted in the bore holes of the needles, and the proximal suture mounting end of the needles was mechanically swaged using a conventional die and swage apparatus. It was observed that all of the needles exhibited cracking in the proximal suture mounting end about the drilled bore hole.

Example 2

Tungsten-Rhenium alloy needles were prepared in a similar manner to the needles of Example 1. The needles were made from an alloy wire having the same composition as that used in Example 1. After laser drilling and prior to suture mounting and mechanical swaging, the needles were heat treated in a furnace at about 1000° C. for about 30 minutes to effectively stress relieve the metal in needles about the laser-drilled bore holes. The same polyester suture was mounted to the heat treated needles and swaged in an identical manner and using the same equipment as in Example 2. None of the needles exhibited cracking in the proximal needle mounting end about the laser-drilled bore hole.

Although this invention has been shown and described with respect to detailed embodiments thereof, it will be understood by those skilled in the art that various changes in form and detail thereof may be made without departing from the spirit and scope of the claimed invention.

What is claimed is:

1. A process for treating surgical needles, comprising:
providing a surgical needle comprising a refractory metal alloy, the surgical needle having a distal piercing end, a proximal suture mounting end and a bore hole that is laser-drilled in the suture mounting end, the bore hole having a cavity and an opening; and,
heat treating at least the suture mounting end by exposing said end to thermal energy for a sufficient amount of time to provide sufficient energy to effectively stress relieve the metal alloy about the bore hole without altering the microstructure and hardness of the metal alloy.

2. The process of claim 1 wherein the refractory alloy metal is Tungsten-Rhenium.

3. The process of claim 1 wherein the refractory alloy is selected from the group consisting of molybdenum, tantalum and niobium.

4. The process of claim 1 comprising the additional steps of mounting an end of a surgical suture in the cavity of the laser-drilled bore hole, and swaging the suture mounting end of the needle.

5. The process of claim 1, wherein the entire needle is heat treated.

6. The process of claim 1, wherein the thermal energy is provided by a laser.

7. The process of claim 1, wherein the thermal energy is provided by a furnace.

8. The process of claim 1, wherein the thermal energy is provided by inductive heating.

9. The process of claim 1, wherein the thermal energy is provided by resistive heating.

10. The process of claim 1, wherein each needle is mounted in a moveable strip, and the strip is moved in front of a laser, which directs a beam to contact at least a section of the needle to provide sufficient thermal energy for a sufficient period of time to effectively heat treat the section of the needle by relieving stress without annealing the metal.

11. The process of claim 7, wherein the needle is maintained at a temperature of about 900° C. to about 1100° C.

12. The process of claim 7, wherein the needle is maintained in the furnace for about 15 to about 60 minutes.

* * * * *